United States Patent
Rollet

(10) Patent No.: US 8,118,875 B2
(45) Date of Patent: Feb. 21, 2012

(54) ORTHOPEDIC DEVICE FOR AN ARTICULAR JOINT

(75) Inventor: Vincent Rollet, Saint Jean le Vieux (FR)

(73) Assignee: Tornier SAS, Saint-Ismier (FR)

( * ) Notice: Subject to any disclaimer, the term of this patent is extended or adjusted under 35 U.S.C. 154(b) by 332 days.

(21) Appl. No.: 12/233,409

(22) Filed: Sep. 18, 2008

(65) Prior Publication Data

US 2009/0076621 A1 Mar. 19, 2009

(30) Foreign Application Priority Data

Sep. 19, 2007 (FR) ...................... 07 57675

(51) Int. Cl.
*A61F 2/40* (2006.01)
(52) U.S. Cl. ................ 623/19.12; 623/18.11; 623/19.11
(58) Field of Classification Search ............... 623/18.11, 623/19.11, 19.12
See application file for complete search history.

(56) References Cited

U.S. PATENT DOCUMENTS

| | | | |
|---|---|---|---|
| 2,203,219 A | | 6/1940 | Jackman |
| 4,093,011 A | | 6/1978 | Bucknavich |
| 4,908,032 A | * | 3/1990 | Keller ......................... 623/23.45 |
| 6,228,120 B1 | * | 5/2001 | Leonard et al. ............. 623/19.12 |
| 7,238,207 B2 | * | 7/2007 | Blatter et al. ............... 623/19.14 |
| 7,651,517 B2 | * | 1/2010 | Konieczynski et al. ...... 606/305 |
| 7,678,150 B2 | * | 3/2010 | Tornier et al. ............... 623/19.13 |

FOREIGN PATENT DOCUMENTS

| | | |
|---|---|---|
| EP | 0679375 A1 | 11/1995 |
| EP | 1088532 A2 | 4/2001 |
| EP | 1679050 A | 7/2006 |
| WO | 2007/039820 A2 | 4/2007 |

OTHER PUBLICATIONS

Search Report dated Dec. 16, 2008 for European Patent Application No. EP 08 16 4669.

* cited by examiner

*Primary Examiner* — David Isabella
*Assistant Examiner* — Seema Swaminathan
(74) *Attorney, Agent, or Firm* — Faegre Baker Daniels LLP

(57) ABSTRACT

An orthopedic device for ball and socket joint reconstruction. The anchor stem is adapted to be anchored in a medullary canal. A proximal portion of the anchor stem includes a threaded hole oriented along a longitudinal axis thereof. Metaphyseal portion includes a proximal end with recess and a longitudinal bore in fluid communication with the recess, and a distal end adapted to interface with the proximal portion of the anchor stem. An anti-rotation structure is preferably located at an interface of the anchoring stem to the metaphyseal portion to prevent rotation of the anchor stem relative to the metaphyseal portion around the longitudinal axis. A fastener is provided to extend through the longitudinal bore and to engage with the threaded hole on the anchor stem to fix the metaphyseal portion to the anchoring stem. The locking assembly is located in the recess and mechanically couples the head of the fastener to the metaphyseal portion to limit rotation of the fastener relative to the metaphyseal portion. An insert with an articular surface is provided that engages with the proximal end of the metaphysical portion and extends over the recess in the metaphyseal portion.

19 Claims, 7 Drawing Sheets

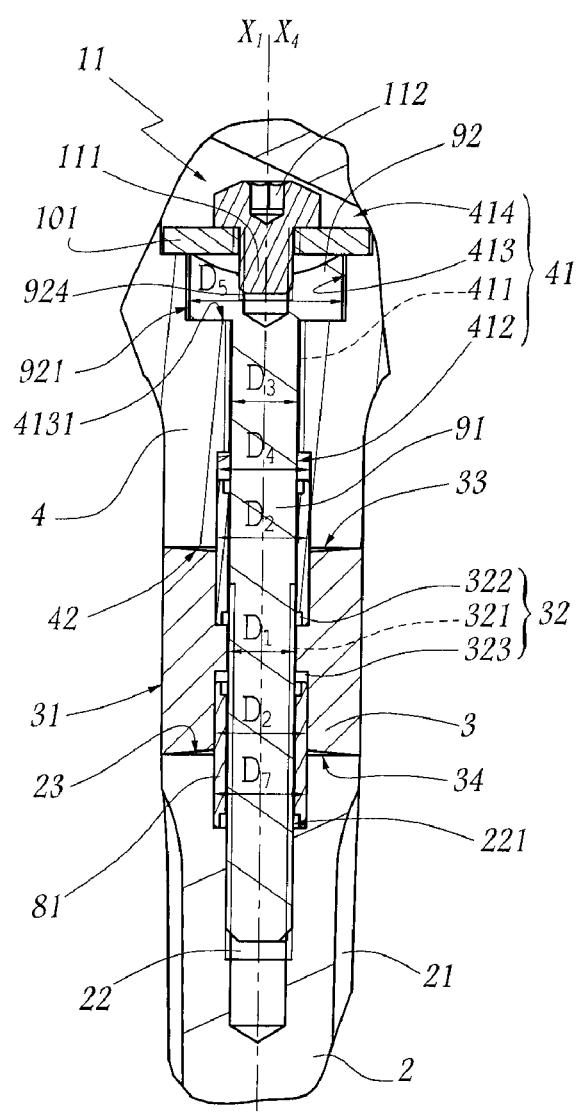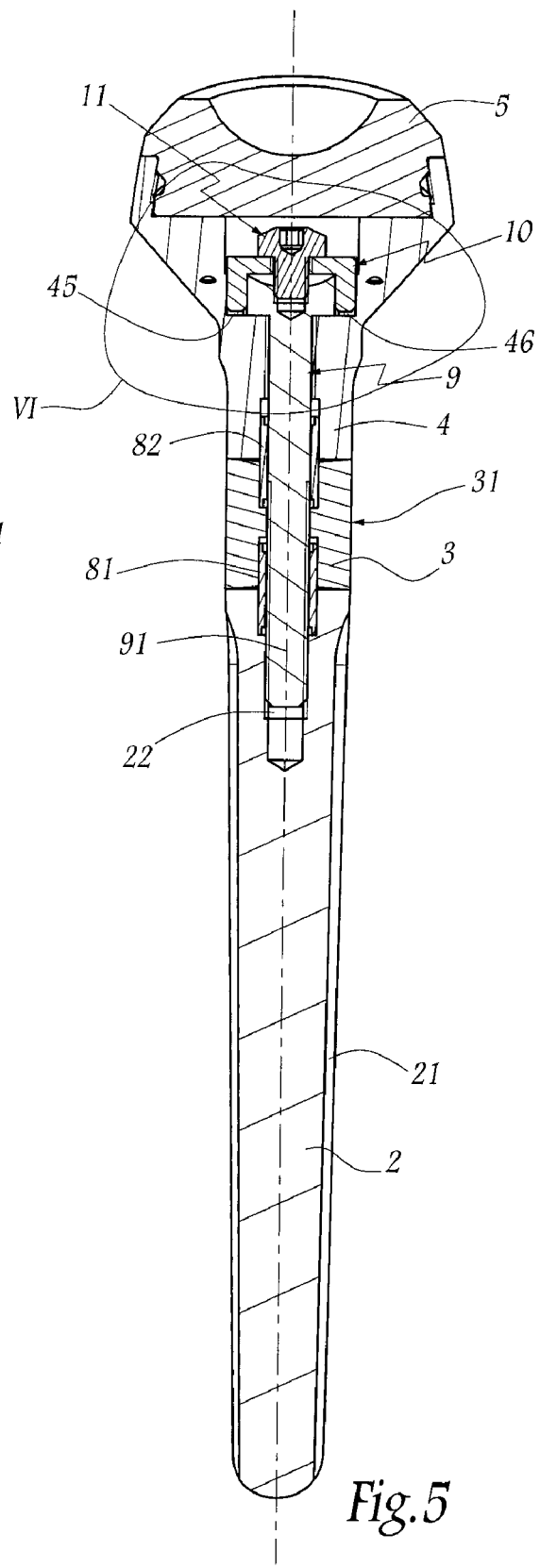

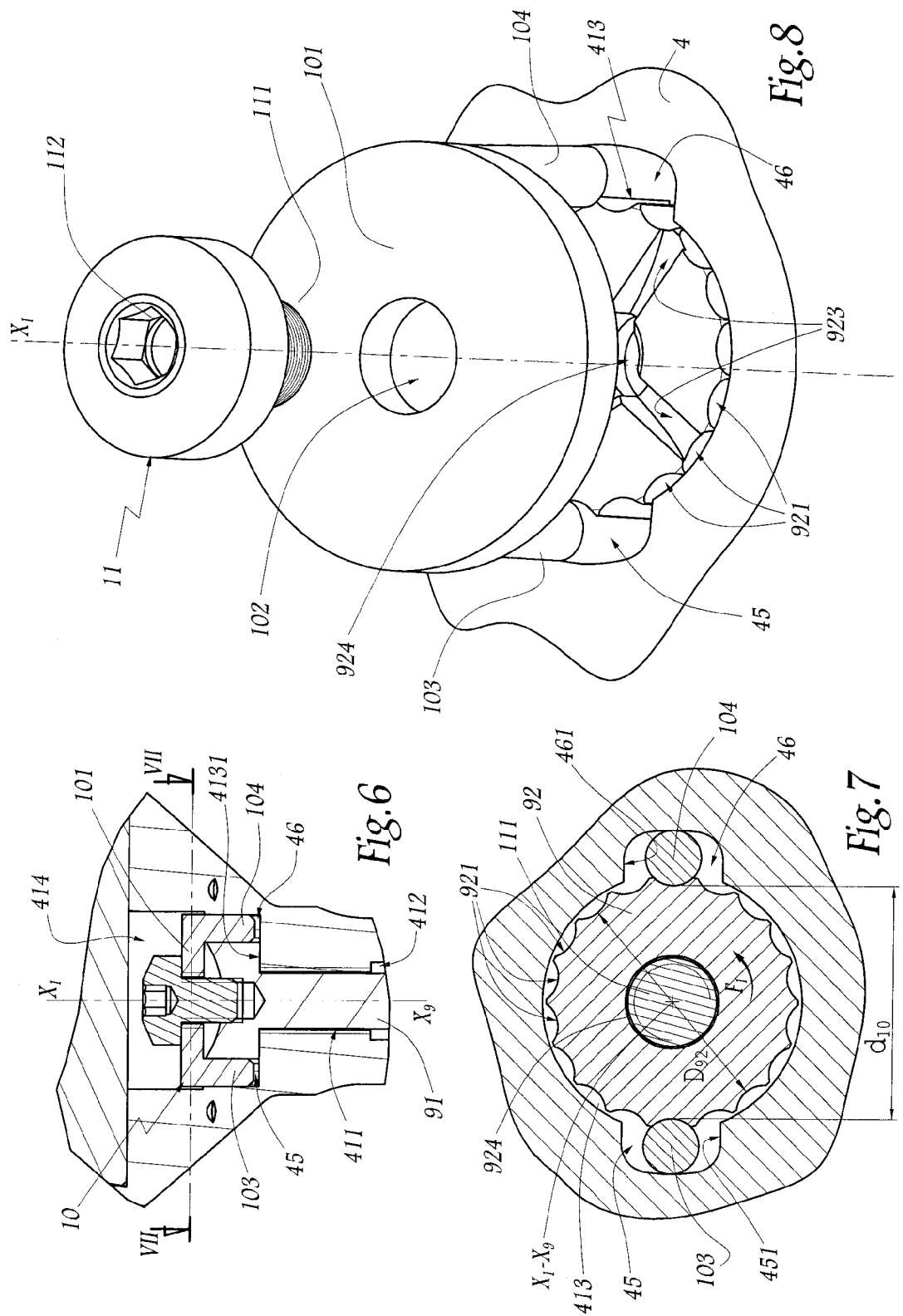

ORTHOPEDIC DEVICE FOR AN ARTICULAR JOINT

CROSS REFERENCE TO RELATED APPLICATIONS

The present application claims priority to French application No. 0757675 filed on Sep. 19, 2007.

FIELD OF THE INVENTION

The present invention relates to an orthopedic device for reconstruction of an articulating joint. The invention also relates to a method for positioning such an orthopedic device.

BACKGROUND OF THE INVENTION

In so far as a prosthesis is installed for a long period of time, it is important to ensure the rigidity and mechanical stability of a prosthesis component. If the screw is not tightened sufficiently during the positioning of the prosthesis, the risk of disassembly of the prosthetic component is aggravated.

EP-A-1 769 050 mentions the principle of locking a screw for controlling the displacement of a wedge-like ring which dilates a widened portion of an anchor stem of a prosthesis. This arrangement is specific to locking by means of a wedge-like ring. The means allowing such locking to be obtained are not described.

BRIEF SUMMARY OF THE INVENTION

The invention is intended more particularly to overcome such disadvantages by providing a new component of an articular prosthesis wherein undesirable unscrewing of the fixing screw may be avoided. Owing to the invention, the locking assembly prevents the screw from becoming loose in an inadvertent manner which ensures the mechanical stability of the orthopedic device. The locking assembly is effective even if the fixing screw is not screwed completely into the corresponding threaded hole.

In one embodiment, the orthopedic device for ball and socket joint reconstruction includes an anchor stem with a distal portion adapted to be anchored in a medullary canal and a proximal portion with a threaded hole oriented along a longitudinal axis of the anchor stem. Metaphyseal portion includes a proximal end with recess and a longitudinal bore in fluid communication with the recess, and a distal end adapted to interface with the proximal portion of the anchor stem. An anti-rotation structure is preferably located at an interface of the anchoring stem to the metaphyseal portion to prevent rotation of the anchor stem relative to the metaphyseal portion around the longitudinal axis. A fastener is provided to extend through the longitudinal bore and to engage with the threaded hole on the anchor stem to fix the metaphyseal portion to the anchoring stem. The locking assembly is located in the recess and mechanically couples the head of the fastener to the metaphyseal portion to limit rotation of the fastener relative to the metaphyseal portion. An insert with an articular surface is provided that engages with the proximal end of the metaphysical portion and extends over the recess in the metaphyseal portion.

According to advantageous but non-compulsory embodiments of the invention, such a orthopedic device may incorporate one or more of the following features.

The locking assembly is provided with at least one projecting member which is capable of being introduced between a head of the screw and the metaphyseal portion adjacent to a housing for receiving the head in an assembled configuration of the orthopedic device.

The locking assembly comprises at least two projecting members which are capable of being introduced simultaneously between the head of the screw and the metaphyseal portion, at one side and the other of the head.

The external radial surface of the head of the screw is provided with reliefs that are capable of co-operating with the projecting member in order to fix the head of the screw and the locking assembly in terms of rotation. Those reliefs are advantageously concave channels which have a shape which complements the shape of the projecting member(s).

In another embodiment, the metaphyseal portion comprises a notch or a number of notches equal to the number of projecting members, and the or each notch opens in the housing for receiving the screw head. Each notch is capable of partially receiving the projecting member or one of the projecting members in an assembled configuration of the orthopedic device.

A fastener is provided for fixing the locking assembly and the screw in a configuration in which the locking assembly prevents rotation of the screw about its longitudinal axis. For example, a threaded hole is provided in the head of the screw and an auxiliary screw is screwed into the threaded hole, pressing the locking assembly against the head of the screw, in a configuration in which the projecting member(s) is/are arranged between the head of the screw and the metaphyseal portion.

In one embodiment, the locking assembly is provided with at least a first relief which is capable of co-operating with at least a corresponding relief of the head of the screw in order to fix the locking assembly and the screw in terms of rotation and with at least a second relief which is capable of co-operating with at least a relief which is fixed relative to the metaphyseal portion in order to lock rotation of the locking assembly.

According to some embodiments, the locking assembly is a ring, and its first relief is internal and the corresponding relief is an external radial relief of the head of the screw. In this case, the first relief of the ring may be a tooth and the corresponding relief of the head of the screw is a notch. In a variant, the ring is provided with an internal peripheral tooth arrangement which forms a plurality of first reliefs, and the head of the screw is provided with an external peripheral tooth arrangement which forms a plurality of reliefs corresponding to the first reliefs of the ring.

According to other embodiments, the locking assembly is a stopper which covers the head of the screw and the first relief is provided at a side of the stopper directed towards the head of the screw, and the corresponding relief is provided at the face of the head of the screw opposite the shank thereof. The head of the screw may carry at least one projection which projects relative to its face opposite the shank, and the stopper is provided with at least one housing for receiving the projection. In a variant, the stopper is provided with a tooth arrangement which forms a plurality of first reliefs and the face of the head of the screw opposite its shank is provided with a tooth arrangement which forms a plurality of reliefs corresponding to the first relief of the stopper.

The second relief of the locking assembly extends over or from the external peripheral edge of the orthopedic device.

A spacer may be arranged between the anchor stem and the metaphyseal portion, the spacer being provided, at its opposing faces directed towards the anchor stem and the metaphyseal portion, respectively, with reliefs which are intended to come into engagement with corresponding reliefs which are provided on the anchor stem and the metaphyseal portion, respectively, preventing rotation of the metaphyseal portion relative to the anchor stem about a longitudinal axis of the spacer.

The invention also relates to an articular prosthesis, particularly a shoulder prosthesis, which comprises an orthopedic device as set out above. Such a prosthesis is more reliable and easier for a surgeon to install than those in the prior art.

The present invention also relates to a method of implanting an orthopedic device for ball and socket joint reconstruction. The method includes the steps of:

inserting a distal portion of an anchor stem in a medullary canal;

engaging a distal end of a metaphyseal portion with a proximal end of the anchor stem;

limiting rotation of the metaphyseal portion relative to the anchor stem;

inserting a distal end of a fastener through a longitudinal bore in the metaphyseal portion;

engaging threads on the distal end of the fastener with corresponding threads on the anchor stem so a head of the fastener is located in a recess on the metaphyseal portion;

mechanically coupling a locking assembly to the head of the fastener and to the metaphyseal portion to limit rotation of the fastener relative to the metaphyseal portion; and engaging an insert to a proximal end of the metaphysical portion so that an articular surface on the insert extends over the recess in the metaphyseal portion.

The invention also relates to a method for positioning an orthopedic device as set out above and, more specifically, a method which comprises steps involving:

a) anchoring the anchor stem in a bone;
b) securing the metaphyseal portion to the anchor stem, with a spacer optionally being interposed;
c) introducing the screw into a longitudinal bore of the metaphyseal portion;
d) screwing the screw into a threaded hole of the anchor stem until the metaphyseal portion is firmly pressed against the stem, with the spacer optionally being interposed;
e) moving a locking assembly into engagement with at least one corresponding relief of a head of the screw and at least one corresponding relief of the metaphyseal portion.

Advantageously, during step e), at least one projecting member of a locking assembly is introduced between a head of the screw and the metaphyseal portion adjacent to a housing for receiving the head.

An additional step may be provided, wherein the locking assembly is immobilised in the configuration in which its projecting member(s) lock(s) the head of the screw in terms of rotation relative to the metaphyseal portion.

In a variant, during step e), at least a first relief of the locking assembly is engaged with a corresponding relief of the screw head in order to fix the locking assembly and the screw in terms of rotation, and at least a second relief of the locking assembly is engaged with a relief which is fixed relative to the metaphyseal portion in order to lock rotation of the locking assembly.

BRIEF DESCRIPTION OF THE SEVERAL VIEWS OF THE DRAWING

The invention will be better understood and other advantages and features thereof will be appreciated more clearly from the following description which is given purely by way of example and with reference to the appended drawings, in which:

FIG. 4 is a view, drawn to an enlarged scale, of detail IV in FIG. 3.

FIG. 5 is a section along line V-V in FIG. 3.

FIG. 6 is a view, drawn to an enlarged scale, of detail VI in FIG. 5.

FIG. 7 is a partial section, drawn to an enlarged scale, along line VII-VII in FIG. 6.

FIG. 8 is a perspective view of the locking assembly for the orthopedic device of FIGS. 1 to 7 during assembly.

DETAILED DESCRIPTION OF THE INVENTION

Figure 1:
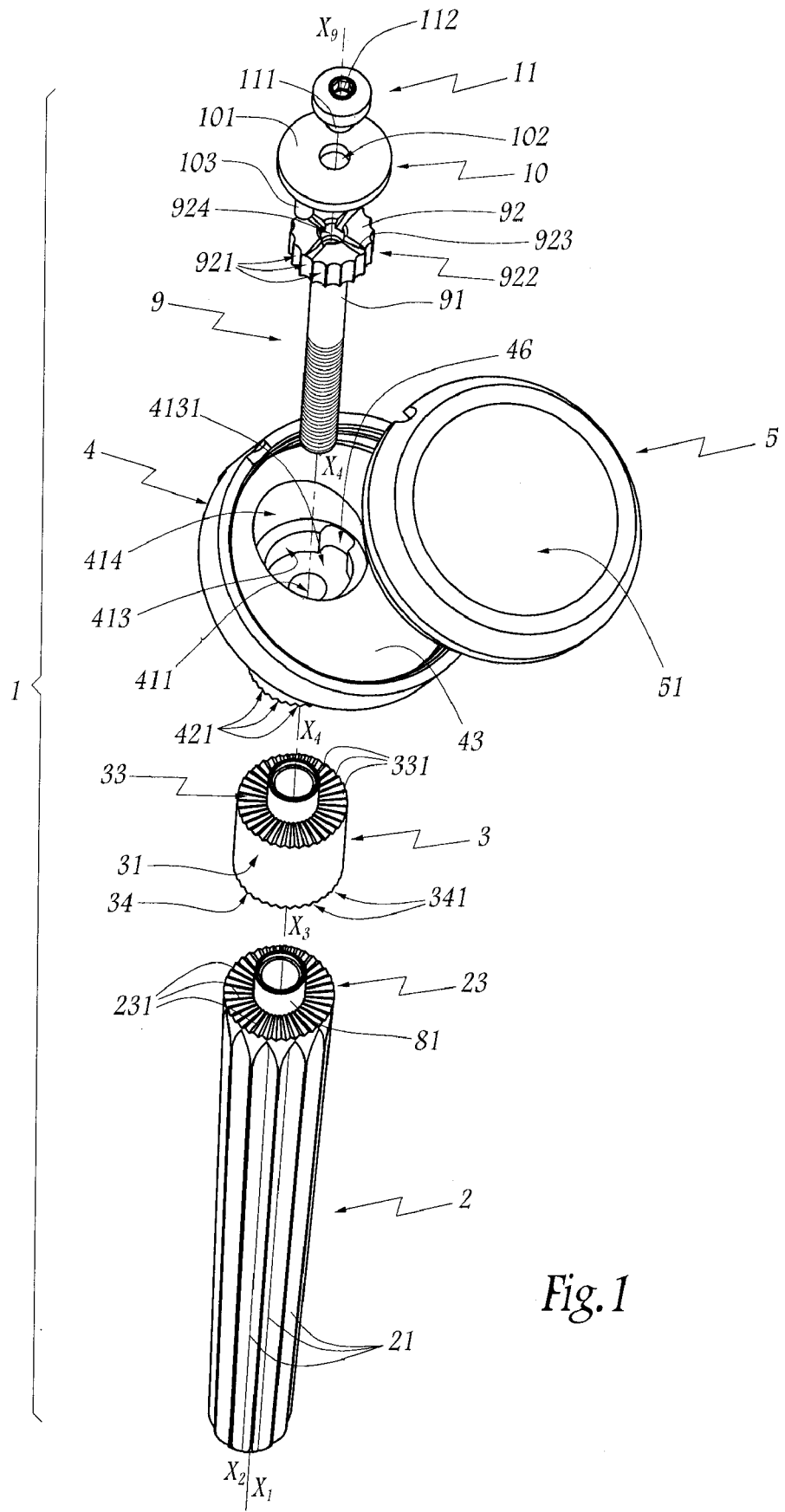
FIG. 1 is a schematic perspective illustration, partially exploded, of a humeral component of a shoulder prosthesis according to an embodiment of the present invention.
Figure 2:
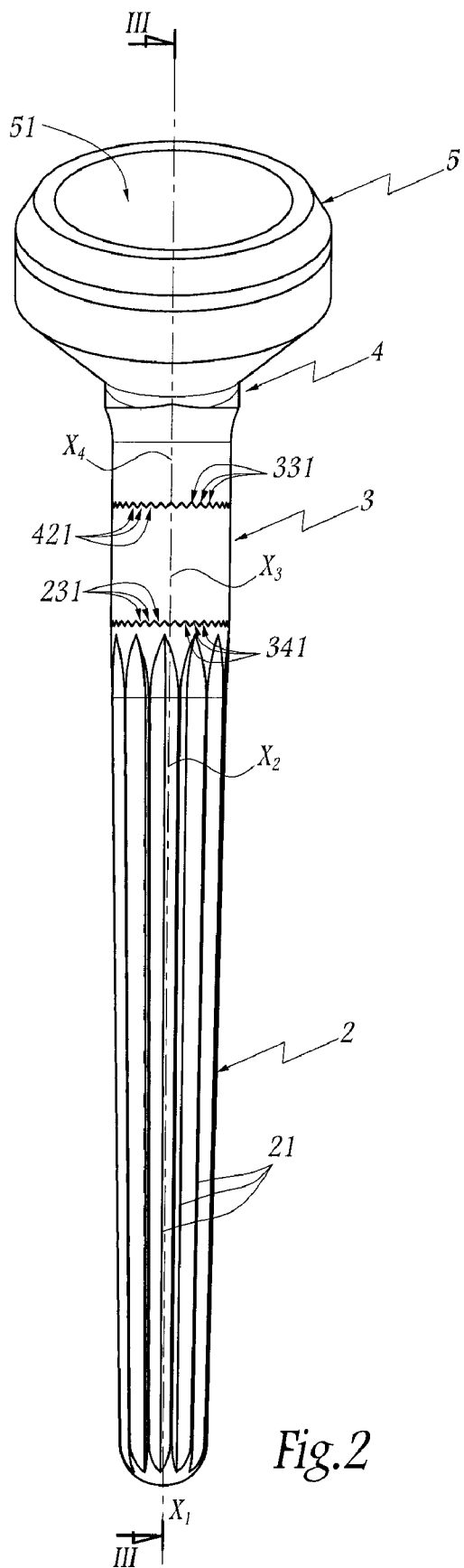
FIG. 2 is a front view of the humeral component of FIG. 1 in an assembled configuration.
Figure 3:
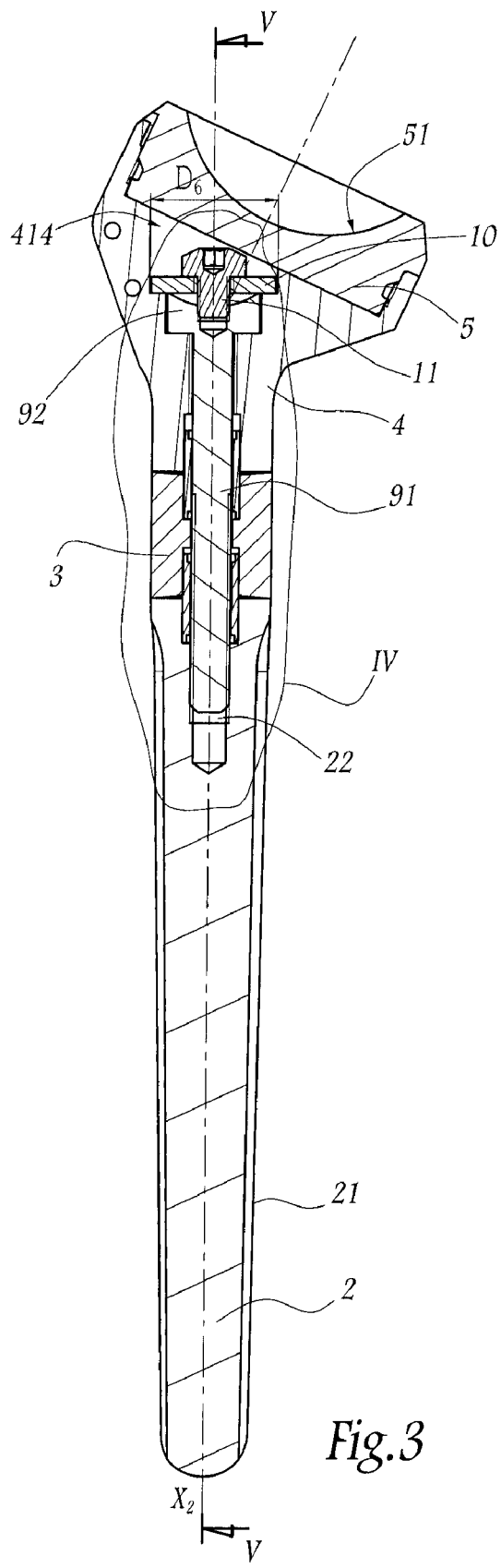
FIG. 3 is a section view of the humeral component of FIG. 2 along line III-III in FIG. 2.

The humeral orthopedic device 1 of a shoulder prosthesis illustrated in FIGS. 1 to 6 comprises an anchor stem 2 which is intended to be introduced and anchored in the medullary canal of a humerus, after resection of its upper end. The stem 2 is provided with external channels 21 which are intended to facilitate its immobilisation in terms of rotation inside the medullary canal. The stem 2 is provided with an axial threaded hole 22 which extends along the longitudinal axis $X_2$ thereof.

The orthopedic device 1 also comprises a spacer 3 which is intended to allow longitudinal adjustment of the orthopedic device 1 taking into consideration the morphology of the patient and the fitting depth of the stem 2 in the humeral medullary canal. The spacer 3 may be selected from a set of spacers having different lengths and different diameters.

The spacer 3 has a cylindrical external radial wall 31 having a circular base. The spacer 3 also has a central bore 32 whose longitudinal axis $X_3$ is intended to be aligned with the axis $X_2$ in an assembled configuration of the orthopedic device 1. The axis $X_3$ is also the axis of symmetry of the surface 31. The bore 32 comprises a median portion 321 which has a first diameter $D_1$ and two portions 322 and 323 which form the opening of the bore 32 at the upper face 33 and the lower face 34 of the spacer 3, respectively. The portions 322 and 323 have the same diameter $D_2$ which is greater than the diameter $D_1$. In this manner, the median portion 321 of the bore 32 forms two shoulders at the bottom of the opening portions 322 and 323.

The face 33 of the spacer 3 is provided with grooves 331 which extend radially around the axis $X_3$. The face 34 is provided with grooves 341 of the same type, only the outline of which is visible in FIGS. 1 and 2.

The upper face 23 of the stem 2, at which the threaded hole 22 opens, is provided with radial grooves 231 which co-operate with the grooves 341 in order to immobilise the spacer 3 relative to the stem 2 in terms of rotation, about the aligned axes $X_2$ and $X_3$, when the surfaces 34 and 23 are in abutment against each other.

The orthopedic device 1 also comprises a metaphyseal portion 4 which forms a support for an insert 5 which defines a concave articular surface 51 which is intended to interact with a convex articular surface which belongs to a glenoid component of the shoulder prosthesis or an intermediate component when use is made of such an intermediate component.

The metaphyseal portion 4 is provided with a longitudinal bore 41 which is centred about an axis $X_4$ which is intended to be aligned with the axes $X_2$ and $X_3$ in an assembled configuration of the orthopedic device 1. The bore 41 comprises a median portion 411 whose diameter is designated $D_3$. The bore 41 also comprises a portion 412 which opens at a face 42 which is intended to be in abutment with the face 33 of the spacer 3 in an assembled configuration of the orthopedic device 1. The diameter of the portion 412 is designated $D_4$. This diameter $D_4$ is substantially equal to the diameter $D_2$. The bore 41 comprises a third portion 413 which adjoins the portion 411 and extends counter to the portion 412 in relation to the portion 411. The diameter of the portion 413 is designated $D_5$. The bore 41 finally comprises a fourth portion 414 which opens at a face 43 of the portion 4 which is inclined relative to the axis $X_4$ and which defines the bottom of the housing for receiving the insert 5 in the portion 4. The diameter of the recess 414 is designated $D_6$. The diameter $D_5$ is greater than the diameter $D_4$ and less than the diameter $D_6$.

The threaded hole 22 does not extend as far as the level of the face 23 of the stem 2, since a countersinking 221 is brought about in the connection zone between the threaded hole 22 and the face 23. The countersinking 221 has a diameter $D_7$ which is substantially equal to the diameter $D_2$. In fact, the portions 322, 323, 412, 413 and 414 of the bores 32 and 41 are also countersinkings which are brought about around the median portions 321 and 411, respectively.

Grooves 421 extend radially over the face 42 of the portion 4 around the axis $X_4$. Those grooves have a shape similar to that of the grooves 331, with which they can be engaged.

When the orthopedic device 1 is assembled, two rings 81 and 82 are secured in the countersinkings 221 and 322, respectively. The rings 81 and 82 allow relative transverse immobilisation of the portions 2, 3 and 4 of the orthopedic device 1 to be brought about during assembly. In practice, the rings 81 and 82 are identical.

When those portions 2, 3 and 4 are in abutment with each other, it is possible to rotate the portion 4 about the axis $X_4$, with the surfaces 23 and 34 or 33 and 42 being moved away from each other in order to adjust the angular orientation of the insert 5 relative to the axes $X_1$, $X_2$ and $X_3$ which define the longitudinal axis $X_1$ of the orthopedic device 1.

When this temporary assembly is brought about, a screw 9 is introduced successively into the bore 41 then the bore 31 and the threaded hole 22. The shank of the screw 9 is designated 91 and its head is designated 92. The longitudinal axis of the shank 91 is designated $X_9$ and is aligned with the axes $X_1$, $X_2$, $X_3$ and $X_4$ in an assembled configuration of the orthopedic device 1.

The head 92 is provided with engagement features 921 which are arranged at its external radial face 922. In the illustrated embodiment the engagement features 921 comprise a plurality of peripheral channels. The head 92 is also provided with four grooves 923 which allow it to co-operate with a flat or cross-head screwdriver in order to move it in rotation about the axis $X_9$ when it is screwed into the threaded hole 22. When the orthopedic device 1 is assembled, the screw 9 is screwed into the threaded hole 22 until its head 92 moves firmly into abutment against the bottom 4131 of the portion 413 of the bore 41. The elements which constitute the orthopedic device 1 are then firmly retained in position relative to each other, the grooves 231 and 341, on the one hand, and 331 and 341, on the other hand, engaged with each other, which contributes to the immobilisation in terms of relative rotation of the portions 2, 3 and 4 about the aligned axes $X_1$, $X_2$, $X_3$ and $X_4$.

In order to prevent accidental unscrewing of the screw 9, under the effect of repeated forces on the orthopedic device 1, and particularly vibrations to which it may be subject, a locking stopper 10 is installed on the head 92. That stopper comprises an annular portion 101 at the centre of which an opening 102 is defined and from which two pins 103 and 104 extend and are diametrically opposed in relation to the opening 102. The pins 103 and 104 extend from the same face of the portion 101. Those pins are separated by a distance $d_{10}$ which is substantially equal to or slightly greater than the diameter $D_{92}$ of the head 92 taken at the level of the bottom of the channels 921. In this manner, the pins 103 and 104 may be arranged at one side and the other of the head 92, being partially engaged in the channels 921, the shape of the channels 921 being selected so as to substantially complement the shape of the internal portions of the pins 103 and 104 directed towards the opening 102. In practice, the channels 921 are cylindrical and have generating lines in the form of an arc of a circle, and the pins 103 and 104 are cylindrical having a generating line which is circular, with a diameter substantially equal to that of the channels. The stopper 10 and the head 92 are fixed in terms of rotation when the pins 103 and 104 are engaged in the channels 921.

The portion 413 of the bore 41 is further bounded by two engagement features 45 and 46, in which the pins 103 and 104 are engaged when they are arranged around the head 92 in position in that portion 413 which forms a housing for receiving the head 92. In the illustrated embodiment, the engagement features 45, 46 comprise notches. The notches 45 and 46 open in the portion 413. In this manner, when the head 92 is received in the housing formed by the portion 413, it may be covered by the stopper 10 with the pins 103 and 104 being partially engaged in two of the channels 921 and the remainder being received in the notches 45 and 46.

If the screw 9 begins to become unscrewed, indicated by the arrow $F_1$ in FIG. 7, the pins 103 and 104 are moved in rotation by the channels about the axis $X_9$ and move into abutment with sides 451 and 461 of the notches 45 and 46, which has the effect of locking the screw 9 in terms of rotation, which cannot be unscrewed any further.

Therefore, the stopper 10 constitutes a first embodiment for locking the screw 9 in terms of rotation relative to the metaphyseal portion 4 and, on that basis, other elements of the orthopedic device 1, that is to say, the stem 2 and the spacer 3.

An auxiliary screw 11 is provided in order to immobilise the stopper 10 on the head 92. To that end, the head 92 is provided with a threaded hole 924 which is aligned with respect to the axis $X_9$ and in which the shank 111 of the screw 11 can be engaged, extending through the opening 102 of the stopper 10. Once the stopper 10 is in position on the head 92, with its pins engaged both in two of the channels 21 and in the notches 45 and 46, it can thereby be immobilised on the head 92 by tightening the auxiliary screw 11 in the threaded hole 924 using a male key which is inserted into a polygonal recess 112 of the screw 11.

In this manner, once the stopper 10 and the auxiliary screw 11 are in position, the screw 9 is not at risk of becoming unscrewed with an angular clearance greater than that corresponding to the displacement of the pins 103 and 104 in order to move into contact with the sides 451 and 461 of the notches 45 and 46. That angular clearance may be relatively small owing to judicious selection of the respective dimensions of the pins 103 and 104 and the notches 45 and 46.

Furthermore, the locking of the screw 9 in terms of rotation is brought about owing to co-operation of the pins 103 and 104, on the one hand, and the notches 45 and 46, on the other hand, even if the screw 9 is not completely tightened in the threaded hole 22. In this manner, the assembly of the orthopedic device 1 is permanent even if the surgeon has not completely tightened the screw in the threaded hole 22.

According to a variant of the invention which is not illustrated, the stopper 10 may be maintained in position on and around the head 92 by other mechanisms than the auxiliary screw 11, in particular by a flange which is provided on the rear surface of the insert 5, which flange then moves into abutment with the stopper 10 when the insert 5 is assembled on the portion 4.

The invention has been illustrated with an orthopedic device 1 provided with a spacer 3. However, it is applicable without such a spacer, the metaphyseal portion 4 being directly in contact with the stem 2. For example, the grooves 231, 341, 331, 421 preferably have the same size, shape and pitch. Consequently, the grooves 231 on the upper face 23 of the stem 2 can engage directly with the grooves 421 on the metaphyseal portion 4.

The grooves 231, 341, 331, 421 comprise an anti-rotation structure at the interface of the components 2, 3, 4, which still permitting the components 2, 3, 4 to be positioned relative to each other in a discrete number of orientations around the longitudinal axes $X_1$, $X_2$, $X_3$, $X_4$ (collectively "X") of the orthopedic device 1. The grooves 231, 341, 331, 421 retain the components 2, 3, 4 in the desired orientation around the longitudinal axis X both before and after the screw 9 is engaged with the stem 2. A variety of other structures are possible to perform the anti-rotation feature of the grooves 231, 341, 331, 421.

The stopper 10 may have only a single locking pin of the same type as the pins 103 and 104 or, conversely, more than two pins, for example, three or four pins which are advantageously distributed regularly around the centre axis of the opening 102. The geometry of the portion 413, in particular the number and the distribution of the notches 45, 46 and the like, is/are adapted to the number and distribution of the pins.

In the embodiments illustrated in FIGS. 9 to 13, elements similar to those of the first embodiment have identical reference numerals.

Figure 10:
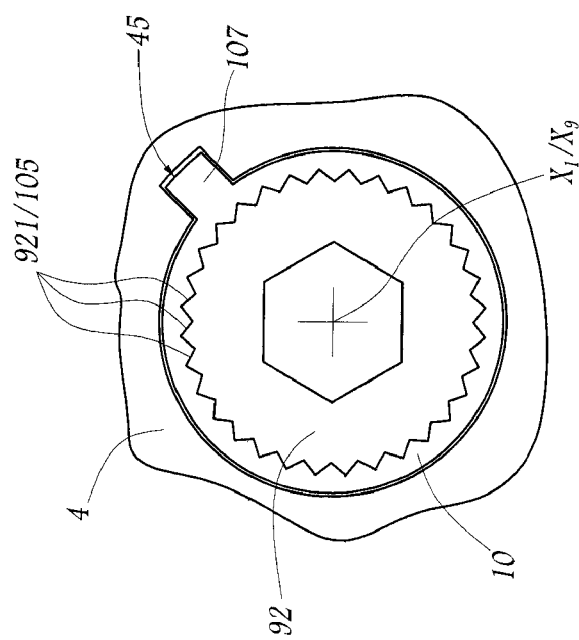
FIG. 10 is a top view of the locking assembly illustrated in FIG. 9 in an assembled configuration of the orthopedic device.
Figure 9:
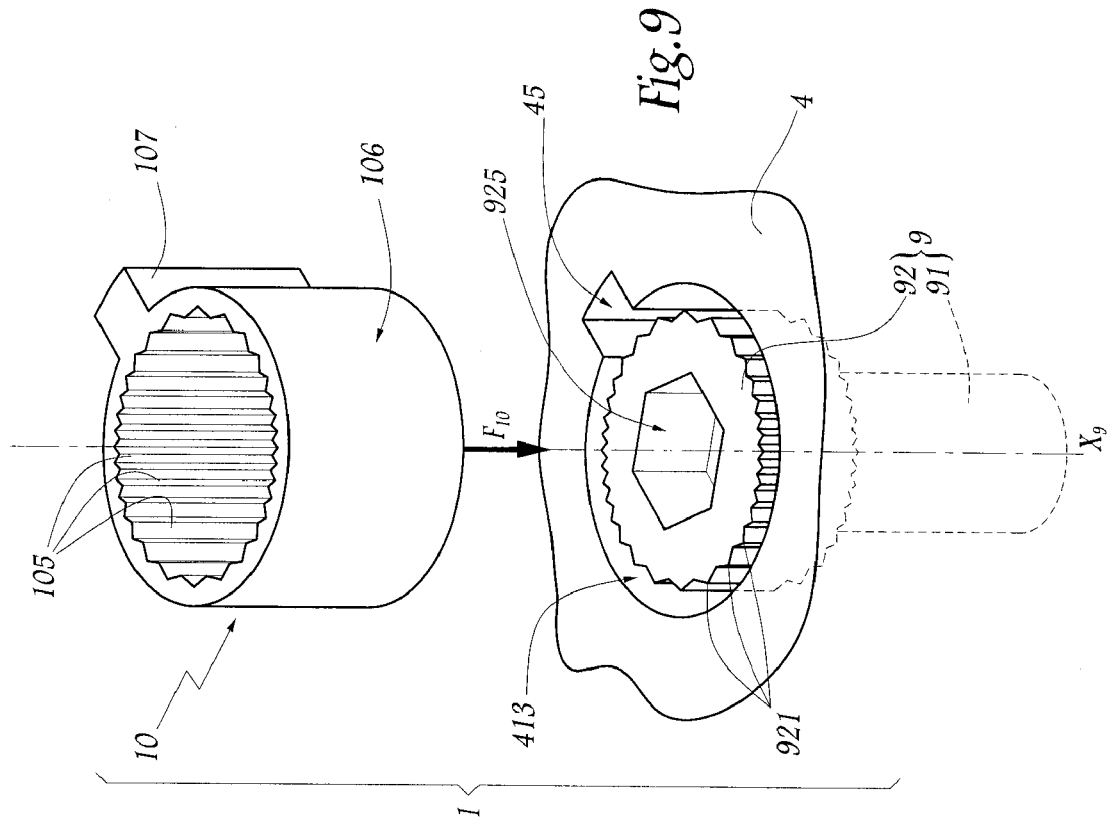
FIG. 9 is a partial perspective view of an alternate locking assembly in according with an embodiment of the present invention.

The orthopedic device 1 partially illustrated in FIGS. 9 and 10 comprise a screw 9 whose shank 91 is supposed to be screwed into an anchor stem which is not illustrated. The head 92 of the screw 9 is provided with an external peripheral tooth arrangement 921, whose teeth generally have a triangular cross-section. In an assembled configuration of the orthopedic device 1, the head 92 is received in a housing 413 which is provided in the metaphyseal portion 4 of the orthopedic device 1. The housing 413 has a circular cross-section with a diameter which is strictly greater than that of the head 92, and a notch 45 is provided in the portion 4 and opens in the housing 413.

Furthermore, a locking ring 10 is provided in order to be introduced into the housing 413 around the head 92, as illustrated by the arrow $F_{10}$ in FIG. 9. The ring 10 is provided with an internal tooth arrangement 105 whose teeth have a triangular cross-section and a shape which complements the teeth of the tooth arrangement 921. The radius of the tooth arrangement 105 is adapted to the radius of the head 92 in such a manner that, when the ring is arranged around the head 92, the tooth arrangements 921 and 105 are engaged, which brings about fixing of the head 92 and the ring 10 in terms of rotation about the axis $X_9$ of the screw 9.

The external radial surface 106 of the ring 10 has a circular cross-section with a diameter which is slightly less than that of the housing 413, with the exception of a portion in which a rib 107 projects radially relative to the surface 106 which forms the external edge of the ring 10. When the ring 10 is positioned around the head 92 in the housing 413, the rib 107 is engaged in the notch 45. The rib 107 extends radially outwards relative to the surface 106 sufficiently in order to lock the ring 10 relative to the portion 4 in terms of rotation about the longitudinal axis $X_1$ of the orthopedic device 1 with which the axis $X_9$ of the screw 9 is in alignment.

In this manner, once the screw 9 is tightened relative to the anchor stem and the portion 4, its rotation about the axis $X_9$ is prevented by the ring 10 whose rib 107 can have only a small angular clearance in the notch 45.

In FIGS. 9 and 10, the reference numeral 925 designates a hexagonal recess for maneuvering the screw 9 using an Allen key.

Figure 11:
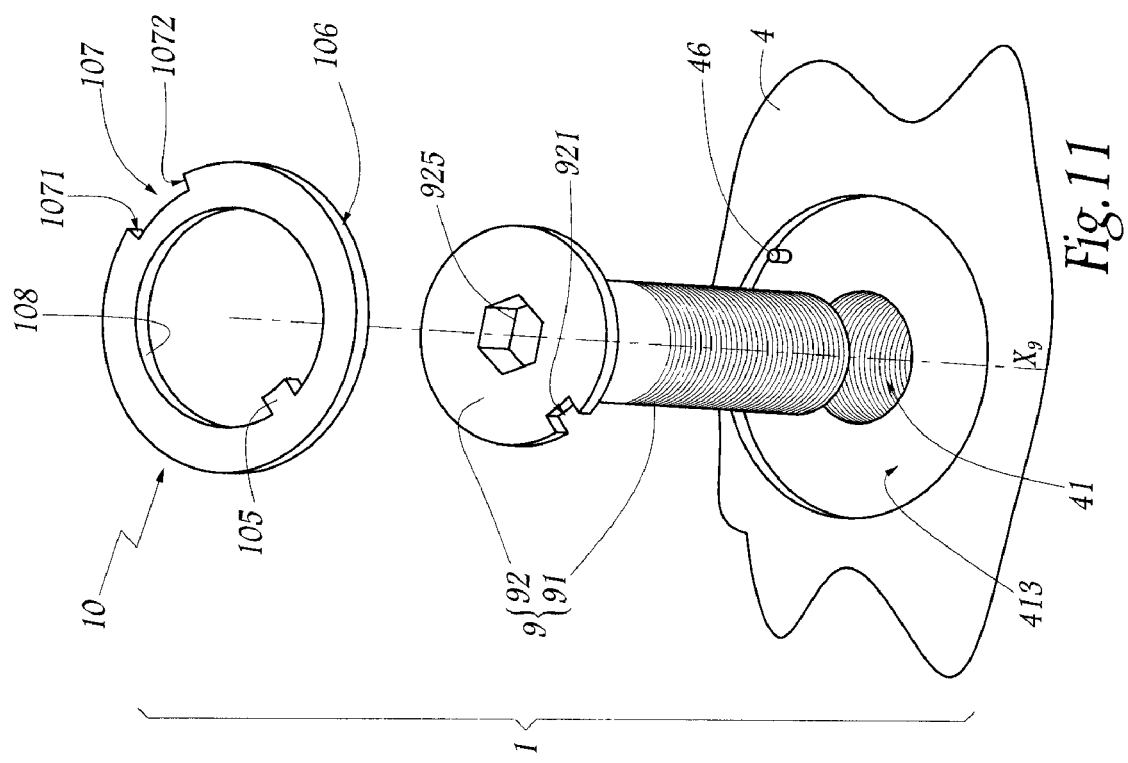
FIG. 11 is a perspective view of an alternate locking assembly in according with an embodiment of the present invention.

In the embodiment of FIG. 11, the screw 9 is provided with a shank 91 and a head 92 whose external peripheral edge is circular, with the exception of a notch 921. The head 92 is also provided with a hexagonal maneuvering recess 925.

The screw 9 is intended to be inserted into a bore 41 whose upper portion 413 forms a housing for receiving the head 92. A pin 46 which extends parallel with a centre axis $X_1$ of the orthopedic device 1 and a longitudinal axis $X_9$ of the screw 9, which are therefore in alignment, is arranged in the housing.

A locking ring 10 is provided so as to be arranged around the head 92 in the housing 413. That ring carries, at its internal edge 108, a tooth 105 whose dimensions allow it to be engaged in the notch 921 with minimal or zero angular clearance. The external peripheral edge 106 of the ring 10 is circular, with the exception of a sector in which a cut-out 107 is provided, which is intended to receive the pin 46 in an assembled configuration of the orthopedic device 1. The edges of the cut-out 107 are designated 1071 and 1072, respectively. When the screw 9 is positioned in the bore 41, with its head 92 being received in the housing 413, it is possible to engage the ring 10 around the head 92 and in the housing 413, with the tooth 105 being arranged in the notch 921, and the cut-out 107 is positioned around the pin 46. Any rotational movement of the screw 9 about the axis $X_9$ is limited owing to the abutment of one of the surfaces 1071 or 1072 against the pin 46.

Figure 12:
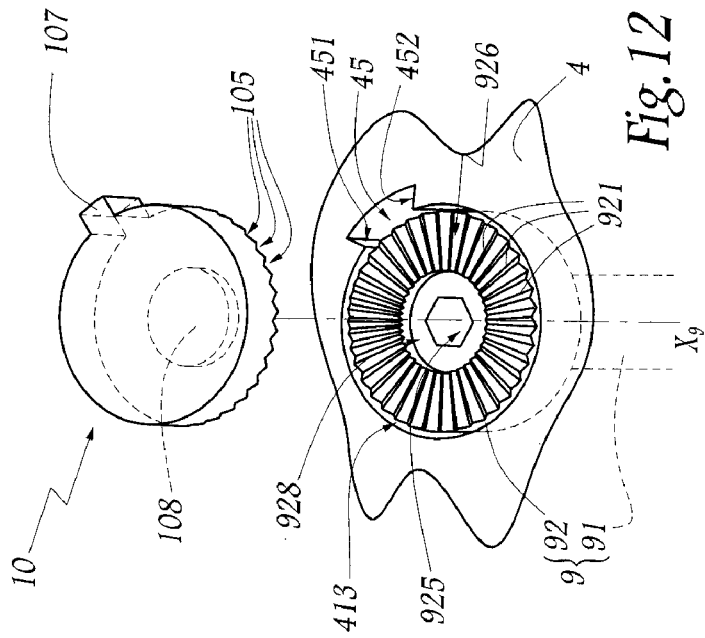
FIG. 12 is a perspective view of an alternate locking assembly in according with an embodiment of the present invention.

In the embodiment of FIG. 12, the screw 9 of the orthopedic device 1 comprises a shank 91 and a head 92 which is provided with a maneuvering recess 925. The head 92 is provided, at its upper face 926 opposite the shank 91, with an annular tooth arrangement 921 which is provided around the centre axis $X_9$ of the screw and the recess 925.

The housing 413 for receiving the head 92 which is provided in the metaphyseal portion 4 generally has a circular cross-section with an extension 45 which communicates with the main portion of the housing 413.

A stopper 10 is further provided so as to be arranged above the head 92 in an assembled configuration of the orthopedic device 1. That stopper comprises a centring portion 108 which is intended to be engaged in a correspondingly shaped recessed housing 928 formed at the face 926. The stopper 10 is further provided with a tooth arrangement 105 whose geometry is adapted to that of the tooth arrangement 921. In this manner, when the portion 108 is engaged in the housing 928, the tooth arrangements 921 and 105 are in engagement and the components 9 and 10 are fixed in terms of rotation about the axis $X_9$.

The peripheral edge of the stopper 10 is provided with a catch 107 which is engaged in the notch 45 in an assembled configuration of the orthopedic device 1. The possibility of angular rotation of the screw 9 about the axis $X_9$ is thereby limited owing to the abutment of the catch 107 against one or other of the edges 451 and 452 of the notch 45.

Figure 13:
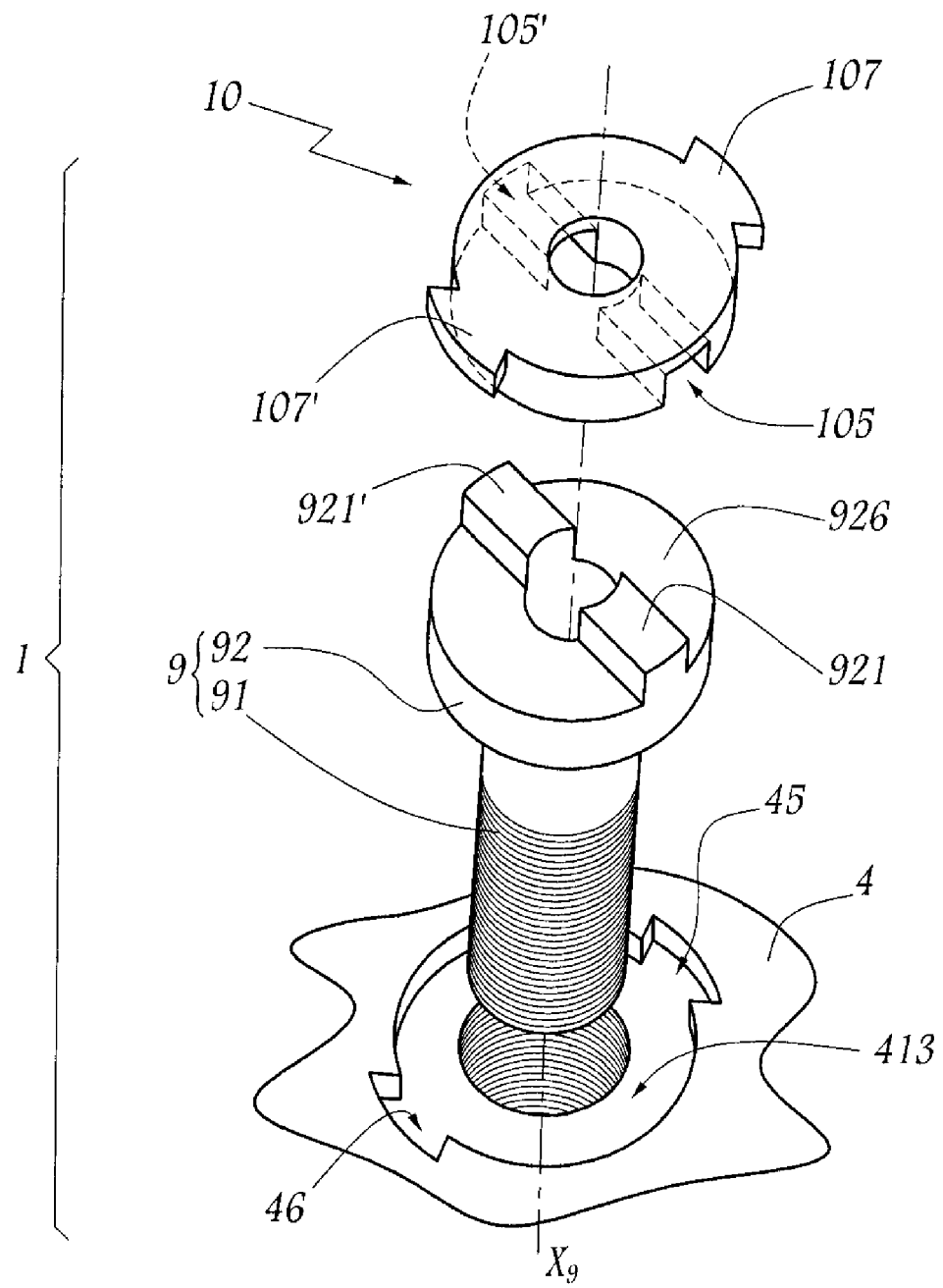
FIG. 13 is a perspective view of an alternate locking assembly in according with an embodiment of the present invention.

In the embodiment of FIG. 13, the screw 9 of the orthopedic device 1 comprises a shank 91 and a head 92 which is provided with two projections 921 and 921' which extend from the face 926 of the head 92 opposite the shank 91.

A stopper 10 is further provided so as to be mounted on the head 92 in an assembled configuration of the orthopedic device 1. That stopper comprises two housings 105 and 105' whose geometry is adapted in order to receive the projections 921 and 921' when the stopper 10 is assembled on the head 92. In this manner, the components 9 and 10 are fixed in terms of rotation.

The stopper 10 is further provided with two fins 107 and 107' which are intended to be engaged in two notches 45 and 46 which are provided in the metaphyseal portion 4 adjacent to a housing 413 for receiving the head 92.

As above, when the stopper 10 is assembled on the head 92, its rotation about the axis $X_9$ is prevented by co-operation of the fins 107 and 107', on the one hand, and the notches 45 and 46, on the other. This allows rotation of the screw 9 to be locked.

In the embodiments illustrated in FIGS. 9 to 13, it is possible to use a member for immobilising the ring or the stopper 10 which is similar to the auxiliary screw 11 of the first embodiment in terms of its function.

The invention has been illustrated in the case of a humeral component of a shoulder prosthesis whose articular surface is concave. However, it may be applied to components whose articular surface is convex. Generally, the invention may be applied to any prosthesis component comprising an anchor stem, irrespective of the geometry of that stem, and a metaphyseal portion which is fixed by a screw, whatever the prosthesis to which it belongs. In particular, the invention also applies to elbow, hip and knee prostheses.

According to a variant of the invention which is not illustrated and which may be applied to all the embodiments, the metaphyseal portion 4 may itself form the articular surface 51.

Where a range of values is provided, it is understood that each intervening value, to the tenth of the unit of the lower limit unless the context clearly dictates otherwise, between the upper and lower limit of that range and any other stated or intervening value in that stated range is encompassed within the inventions. The upper and lower limits of these smaller ranges which may independently be included in the smaller ranges is also encompassed within the inventions, subject to any specifically excluded limit in the stated range. Where the stated range includes one or both of the limits, ranges excluding either both of those included limits are also included in the inventions.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present inventions are not entitled to antedate such publication by virtue of prior invention. Further, the dates of publication provided may be different from the actual publication dates which may need to be independently confirmed.

Other embodiments of the invention are possible. Although the description above contains many specific examples, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims.

What is claimed is:

1. An orthopedic device for ball and socket joint reconstruction, the orthopedic device comprising:
    an anchor stem comprising a distal portion adapted to be anchored in a medullary canal and a proximal portion with a threaded hole oriented along a longitudinal axis of the anchor stem;
    a metaphyseal portion comprising a proximal end with a recess and a longitudinal bore in fluid communication with the recess, and a distal end adapted to interface with the proximal portion of the anchor stem;
    an anti-rotation structure located at an interface of the anchor stem to the metaphyseal portion that prevents rotation of the anchor stem relative to the metaphyseal portion around the longitudinal axis;
    a fastener comprising a proximal end with a head and a threaded distal end, the fastener adapted to extend through the longitudinal bore and engage with the threaded hole on the anchor stem to fix the metaphyseal portion to the anchoring stem;
    a locking assembly adapted to be located in the recess to mechanically couple the head of the fastener to the metaphyseal portion to limit rotation of the fastener relative to the metaphyseal portion; and an insert comprising an articular surface, the insert adapted to engage with the proximal end of the metaphyseal portion and to extend over the recess in the metaphyseal portion.

2. The orthopedic device of claim 1 comprising a ring oriented concentric with the longitudinal axis and telescopically engaged with the proximal portion of the anchor stem and the distal end of the metaphyseal portion.

3. The orthopedic device of claim 1 wherein the anti-rotation structure comprises:

a plurality of grooves on a proximal end of the stem; and
a plurality of corresponding grooves on the distal end of the metaphyseal portion.

4. The orthopedic device of claim 1 wherein the head of the fastener comprises a non-circular cross-section.

5. The orthopedic device of claim 1 wherein the recess in the metaphyseal portion and the head of the fastener each comprise at least one engagement feature, and the locking assembly comprises at least one projecting member shaped to mechanically couple with engagement features on both the recess and the head of the fastener.

6. The orthopedic device of claim 1 wherein the locking assembly comprises at least one projecting member that is shaped to be introduced simultaneously between the head of the fastener and a side surface of the recess on the metaphyseal portion.

7. The orthopedic device of claim 1 wherein an external radial surface of the head of the fastener includes a plurality of recesses that engage with a projecting member on the locking assembly.

8. The orthopedic device of claim 1 wherein a projecting member on the locking assembly simultaneously engages with at least one of a plurality of concave channels on an external radial surface of the head of the fastener and a notch in a side surface of the recess in the metaphyseal portion.

9. The orthopedic device of claim 8 wherein partial engagement of the projecting member with one of the plurality of concave channels limits rotation of the head relative to the metaphyseal portion.

10. The orthopedic device of claim 1 wherein the recess in the metaphyseal portion comprises at least one notch shaped to engage with a projecting member on the locking assembly.

11. The orthopedic device of claim 1 wherein a projecting member on the locking assembly simultaneously engages with a relief on an external radial surface on the head of the fastener and a relief in the metaphyseal portion to limit rotation of the head relative to the metaphyseal portion.

12. The orthopedic device of claim 1 comprising an auxiliary screw engaged with a threaded hole in the head of the fastener to secure the locking assembly to the orthopedic device.

13. The orthopedic device of claim 1 wherein the locking assembly comprises a ring with a plurality of internal engagement structures configured to engage with corresponding engagement structures on an external radial surface of the head of the fastener, and an external engagement structure adapted to mechanically couple with the metaphyseal portion.

14. The orthopedic device of claim 13 wherein the plurality of internal engagement structures and corresponding engagement structures on the external radial surface of the head comprise a complementary tooth arrangement.

15. The orthopedic device of claim 1 wherein the locking assembly comprises a stopper that covers the head of the screw, wherein the stopper comprises an engagement structure on a side directed towards the head of the fastener, and a corresponding engagement structure on the head of the fastener.

16. The orthopedic device of claim 1 wherein the anti-rotation structure is integrally formed in the proximal portion of the anchor stem and the distal end of the metaphyseal portion.

17. The orthopedic device of claim 1 comprising a spacer adapted to mechanically engage with the anti-rotation structure at the interface between the metaphyseal portion and the anchor stem.

18. The orthopedic device of claim 1 wherein the articular surface comprises a concave surface for a reverse shoulder prosthesis.

19. An orthopedic device for ball and socket joint reconstruction, the orthopedic device comprising:

an anchor stem comprising a distal portion adapted to be anchored in a medullary canal and a proximal portion with a threaded hole oriented along a longitudinal axis of the anchor stem;

a metaphyseal portion comprising a proximal end with a recess and a longitudinal bore in communication with the recess, and a distal end adapted to interface with the proximal portion of the anchor stem;

a fastener comprising a proximal end with a head and a threaded distal end, the fastener adapted to extend through the longitudinal bore and engage with the threaded hole on the anchor stem to fix the metaphyseal portion to the anchoring stem;

a locking assembly adapted to be located in the recess to mechanically couple the head of the fastener to the metaphyseal portion to limit rotation of the fastener relative to the metaphyseal portion, wherein the locking assembly comprises at least one projecting member that is shaped to be introduced simultaneously between the head of the fastener and a side surface of the recess on the metaphyseal portion; and an insert comprising an articular surface, the insert adapted to engage with the proximal end of the metaphyseal portion and to extend over the recess in the metaphyseal portion.

* * * * *